(12) United States Patent
Reed et al.

(10) Patent No.: US 10,126,272 B2
(45) Date of Patent: Nov. 13, 2018

(54) SYSTEMS AND METHODS FOR ULTRASONIC INSPECTION OF TURBINE COMPONENTS

(71) Applicant: General Electric Company, Schenectady, NY (US)

(72) Inventors: Francis Alexander Reed, Schenectady, NY (US); Robert William Bergman, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 180 days.

(21) Appl. No.: 14/982,783

(22) Filed: Dec. 29, 2015

(65) Prior Publication Data

US 2017/0184549 A1    Jun. 29, 2017

(51) Int. Cl.
*G01N 29/06*    (2006.01)
*F01D 21/00*    (2006.01)
(Continued)

(52) U.S. Cl.
CPC ....... *G01N 29/0654* (2013.01); *F01D 21/003* (2013.01); *G01M 5/0016* (2013.01);
(Continued)

(58) Field of Classification Search
CPC ..... G01N 2291/023; G01N 2291/0289; G01N 2291/106; G01N 29/0654; F01D 21/003; F05D 2260/80; G01M 13/00
See application file for complete search history.

(56) References Cited

U.S. PATENT DOCUMENTS 4,242,912 A * 1/1981 Burckhardt ............... A61B 8/14
310/334
5,111,696 A * 5/1992 Lund .................. G01N 29/0609
702/39
(Continued)

OTHER PUBLICATIONS

Holmes, et al., "Post-Processing of the Full Matrix of Ultrasonic Transmit-Receive Array Data for Non-Destructive Evaluation," NDT&E International 38 (2005) pp. 701-711.
(Continued)

*Primary Examiner* — Natalie Huls
(74) *Attorney, Agent, or Firm* — Eversheds-Sutherland (US) LLP

(57) ABSTRACT

Embodiments of the disclosure relate to ultrasonic inspection of turbine components. In one embodiment, a method for ultrasonic inspection of a turbine component can include mounting at least one array of transducer elements to the turbine component, (a) separately pulsing a transducer element of the at least one array of transducer elements to transmit a signal to the turbine component, (b) capturing reflected signals from the turbine component at each transducer element in the at least one array of transducer elements, repeating (a) and (b) for each of the other transducer elements in the at least one array of transducer elements, maintaining a constant relative position of the array of transducer elements with respect to the turbine component, analyzing the captured reflected signals using a computer, generating an image of the interior volume of the turbine component by reconstruction of the captured reflected signals and based at least in part on detecting an anomaly in the image of the interior volume of the turbine component, identifying at least one defect or failure in the turbine component.

17 Claims, 5 Drawing Sheets

(51) Int. Cl.
*G01M 5/00* (2006.01)
*G01N 29/04* (2006.01)
*G01N 29/26* (2006.01)

(52) U.S. Cl.
CPC ........ *G01M 5/0033* (2013.01); *G01M 5/0066* (2013.01); *G01N 29/043* (2013.01); *G01N 29/069* (2013.01); *G01N 29/262* (2013.01); *F05D 2260/80* (2013.01); *G01N 2291/044* (2013.01); *G01N 2291/106* (2013.01); *G01N 2291/2693* (2013.01)

(56) References Cited

U.S. PATENT DOCUMENTS

| | | | | |
|---|---|---|---|---|
| 5,408,884 | A * | 4/1995 | Sabourin | G01N 29/043 73/620 |
| 6,082,198 | A * | 7/2000 | Sabourin | G01N 29/262 73/628 |
| 7,017,414 | B2 * | 3/2006 | Falsetti | G01N 29/11 73/600 |
| 7,174,788 | B2 * | 2/2007 | Czerw | G01N 29/265 73/620 |
| 7,428,842 | B2 * | 9/2008 | Fair | G01N 29/262 73/602 |
| 7,500,396 | B2 * | 3/2009 | Bentzel | G01N 29/043 73/628 |
| 7,779,695 | B2 * | 8/2010 | Clossen-von Lanken Schulz | G01N 29/07 73/622 |
| 8,438,929 | B2 * | 5/2013 | Metala | G01M 13/00 73/593 |
| 8,515,711 | B2 * | 8/2013 | Mitchell | F01D 21/003 702/116 |
| 8,525,831 | B2 * | 9/2013 | Zhang | G01N 29/0654 345/419 |
| 9,482,645 | B2 * | 11/2016 | Freda | G01N 29/11 |
| 2009/0307628 | A1 * | 12/2009 | Metala | G06T 7/0006 715/782 |
| 2011/0277549 | A1 * | 11/2011 | Frederick | G01N 29/07 73/627 |
| 2013/0308419 | A1 * | 11/2013 | Singh | G01N 29/043 367/7 |
| 2014/0060188 | A1 * | 3/2014 | Singh | G01N 29/12 73/579 |
| 2014/0238136 | A1 * | 8/2014 | Ten Grotenhuis | G01N 29/0654 73/592 |
| 2015/0212051 | A1 * | 7/2015 | Bannouf | G01S 15/8977 702/191 |
| 2016/0011305 | A1 * | 1/2016 | Koptenko | G10K 11/341 367/7 |
| 2016/0266069 | A1 * | 9/2016 | Jenkins | G01N 29/043 |

OTHER PUBLICATIONS

Drinkwater, Bruce W. and Wilcox, Paul D., "Ultrasonic Arrays for Non-Destructive Evaluation: A Review," NDT&E International 39 (2006) pp. 525-541.

Advances in Phased Array Ultrasonic Technology Applications, Olympus NDT, (2007) pp. 5-55.

* cited by examiner

3-D View of Inspection region (1)
230

Possible Scanning configuration
240

SYSTEMS AND METHODS FOR ULTRASONIC INSPECTION OF TURBINE COMPONENTS

This disclosure relates to turbine components, and more particularly, to systems and methods for ultrasonic inspection of turbine components.

BACKGROUND OF THE DISCLOSURE

A turbine section generally includes moving parts that encounter hot fluids (steam in the case of a steam turbine and hot gases in the case of a gas turbine). These moving parts can be affected by operating conditions of the turbine, for example, high temperatures, high pressures, high-speed rotations, and so forth. As a result, buckets, nozzles, airfoils, blades, and other hot gas path components are subject to failures, such as creep, fatigue, degradation, migration, liberation, shrouding, cracking, and so forth.

As can be expected, these various parts may deteriorate or fail over time and may need to be replaced when the overall performance of the turbine suffers as a result of a deteriorated or failed part. However, it is generally undesirable to wait for a part to malfunction or to fail completely before replacing the failed part, especially if such a replacement necessitates shutting down the turbine for an extended period of time. Consequently, in order to avoid such a situation, a turbine and its components need to undergo periodic testing in order to assess whether they have been subjected to failures and if they need to be repaired or replaced.

Conventional inspection methods can provide turbine inspectors with various information for evaluating the condition of a turbine component. However, the amount of information needed to evaluate a relatively large component such as a steam turbine rotor or other such part may be time consuming to process. Furthermore, the time to evaluate and process the amount of information gathered from a relatively large component such as a steam turbine rotor or other such part can add to the downtime of the turbine, which can be expensive.

BRIEF DESCRIPTION OF THE DISCLOSURE

Some or all of the above needs and/or problems may be addressed by certain embodiments of the disclosure. Embodiments of the disclosure are generally directed to systems and methods for ultrasonic inspection of turbine components. According to one example embodiment of the disclosure, a method for ultrasonic inspection of a turbine component can include mounting at least one array of transducer elements to the turbine component. Each element in each array of transducer elements can be pulsed separately to transmit a signal to the turbine component. The signals can be reflected from the turbine component and captured at each transducer element. The array(s) of transducer elements can be maintained at a constant position relative to the turbine component. Based at least in part on the captured reflected signals, at least one defect or failure can be identified in the turbine component.

According to another example embodiment of the disclosure, there is disclosed a system for ultrasonic inspection of a turbine component. The system may include at least one array of transducer elements mounted on a turbine component. Each transducer element in the array can be pulsed separately to transmit a signal to the turbine component. The reflected signals from the turbine component can be captured at each transducer element. The array of transducer elements mounted on the turbine component can be maintained in a constant relative position with respect to the turbine component. The system can further include a computer that can analyze the captured reflected signals, and generate an image of the interior volume of the turbine component by reconstruction of the captured reflected signals. Based at least in part on the captured reflected signals, at least one defect or failure can be identified in the turbine component.

According to another example embodiment of the disclosure, a method for ultrasonic inspection of a turbine component can include mounting at least one array of transducer elements to the turbine component. Each element in each array of transducer elements is pulsed separately to transmit a signal to the turbine component. The signals reflected from the turbine component are captured at each transducer element. The array(s) of transducer elements are maintained at a constant position relative to the turbine component. The captured reflected signals are analyzed using a computer, where an image of the interior volume of the turbine component is generated by reconstruction of the captured reflected signals. Based at least in part on detecting an anomaly in the image of the interior volume of the turbine component, at least one defect or failure is identified in the turbine component.

Other embodiments and aspects of the disclosure will become apparent from the following description taken in conjunction with the following drawings.

BRIEF DESCRIPTION OF THE DRAWINGS

Figure 1:
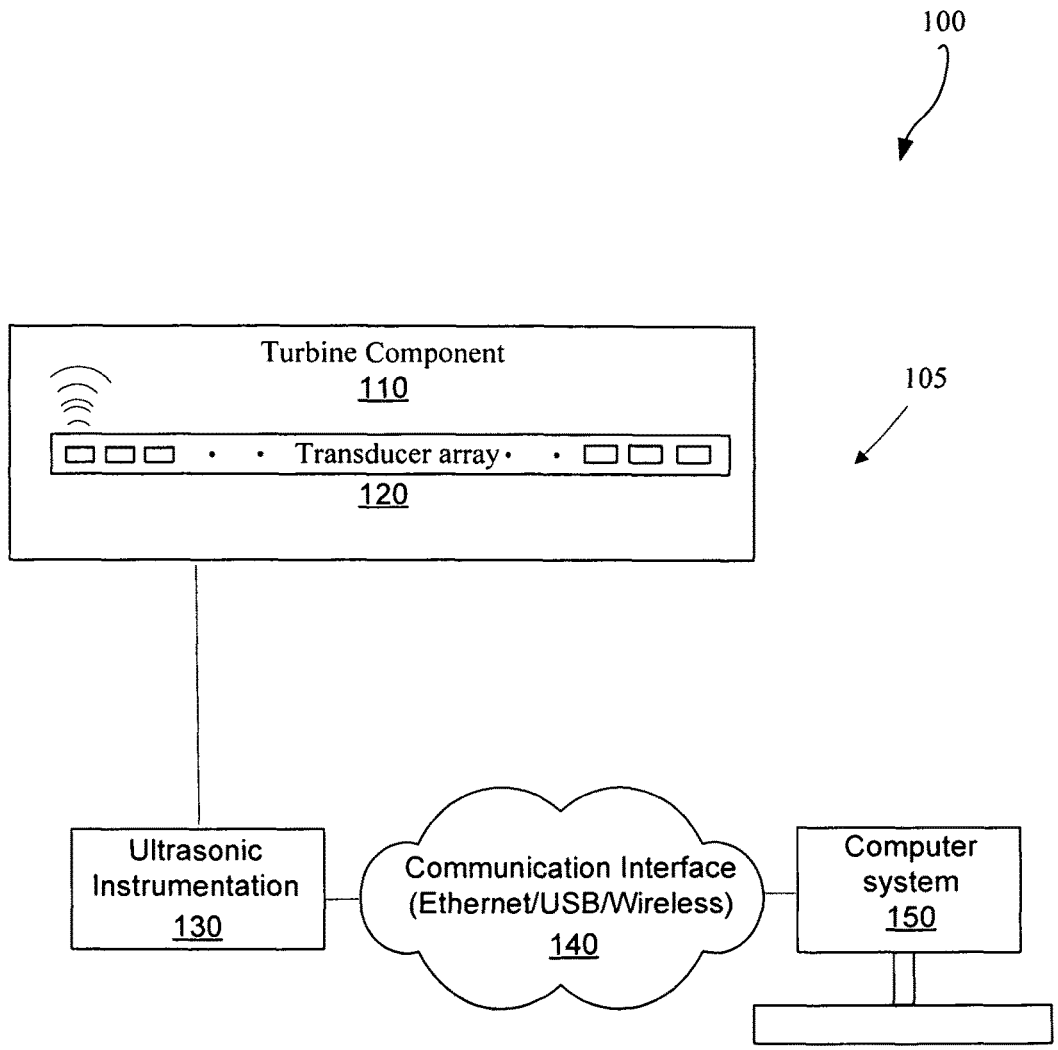

Having thus described the disclosure in general terms, reference will now be made to the accompanying drawings, which are not necessarily drawn to scale, and wherein:

FIG. 1 illustrates an example ultrasonic inspection system for inspecting turbine components in accordance with certain embodiments of the disclosure.

Figure 2A:
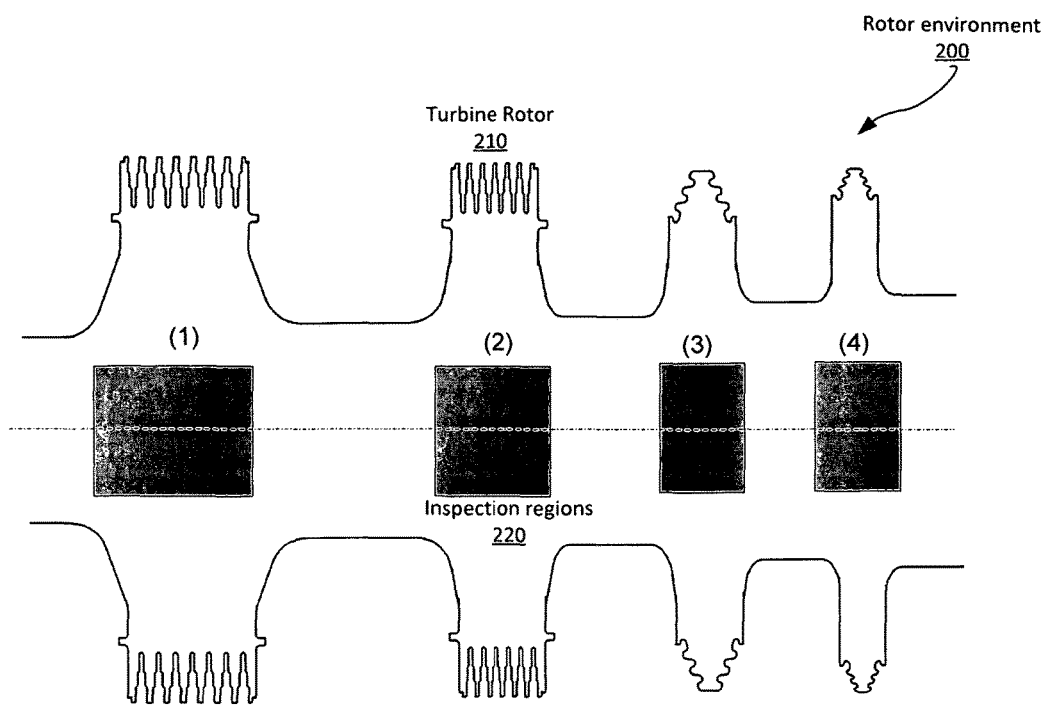
Figure 2B:
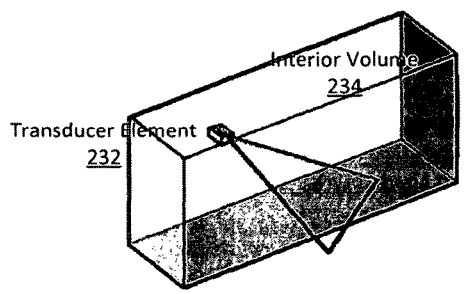
Figure 2C:
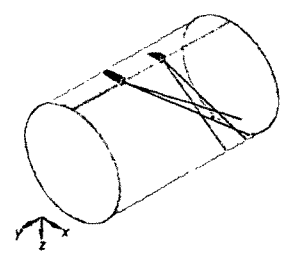

FIGS. 2A-2C illustrate an example turbine rotor with inspection regions and example scanning configurations for ultrasonic inspection of a turbine component in accordance with certain embodiments of the disclosure.

Figure 3A:
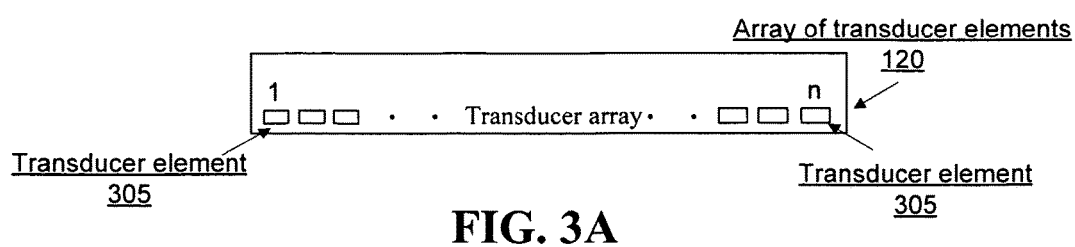
Figure 3B:
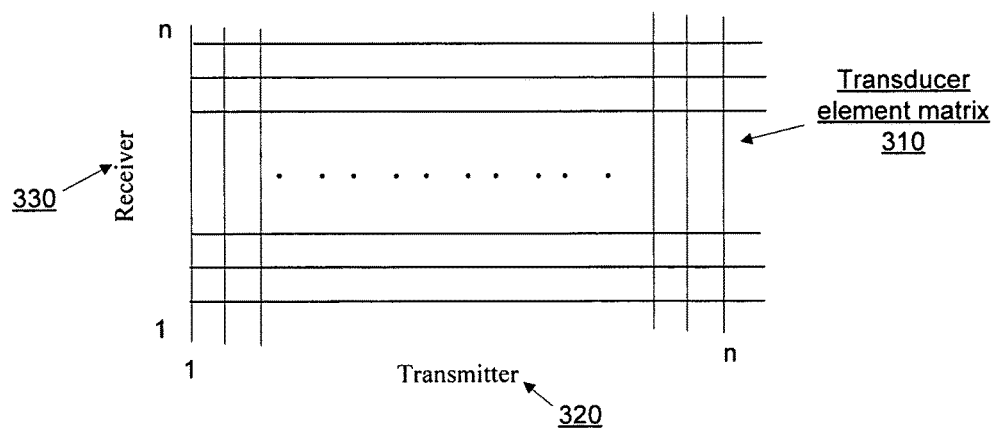

FIG. 3A-3B illustrate an example transducer element array and matrix configured for performance of a full matrix capture ultrasonic inspection of a turbine component in accordance with certain embodiments of the disclosure.

Figure 4:
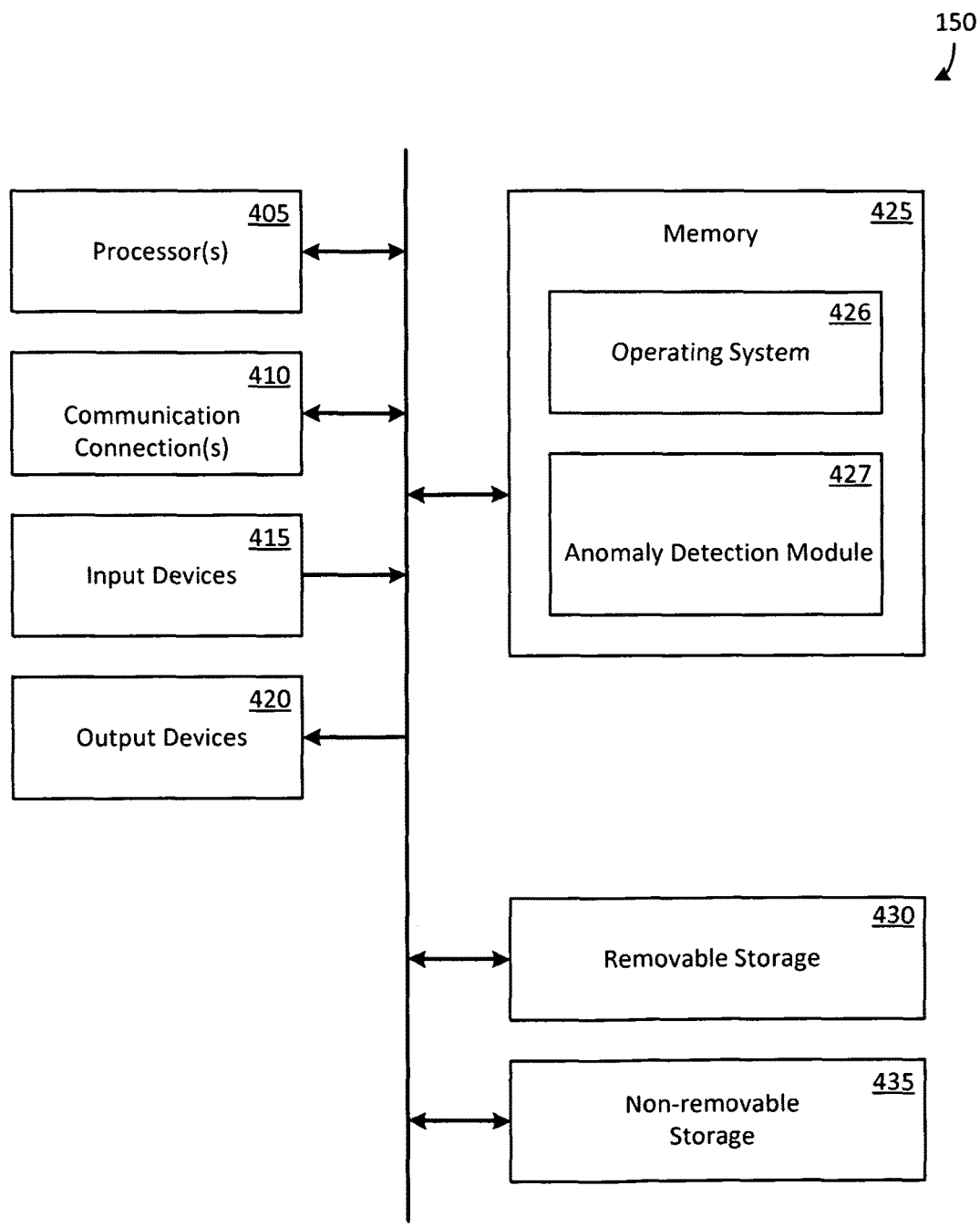

FIG. 4 illustrates an example computer system configured for ultrasonic inspection of a turbine component in accordance with certain embodiments of the disclosure.

Figure 5:
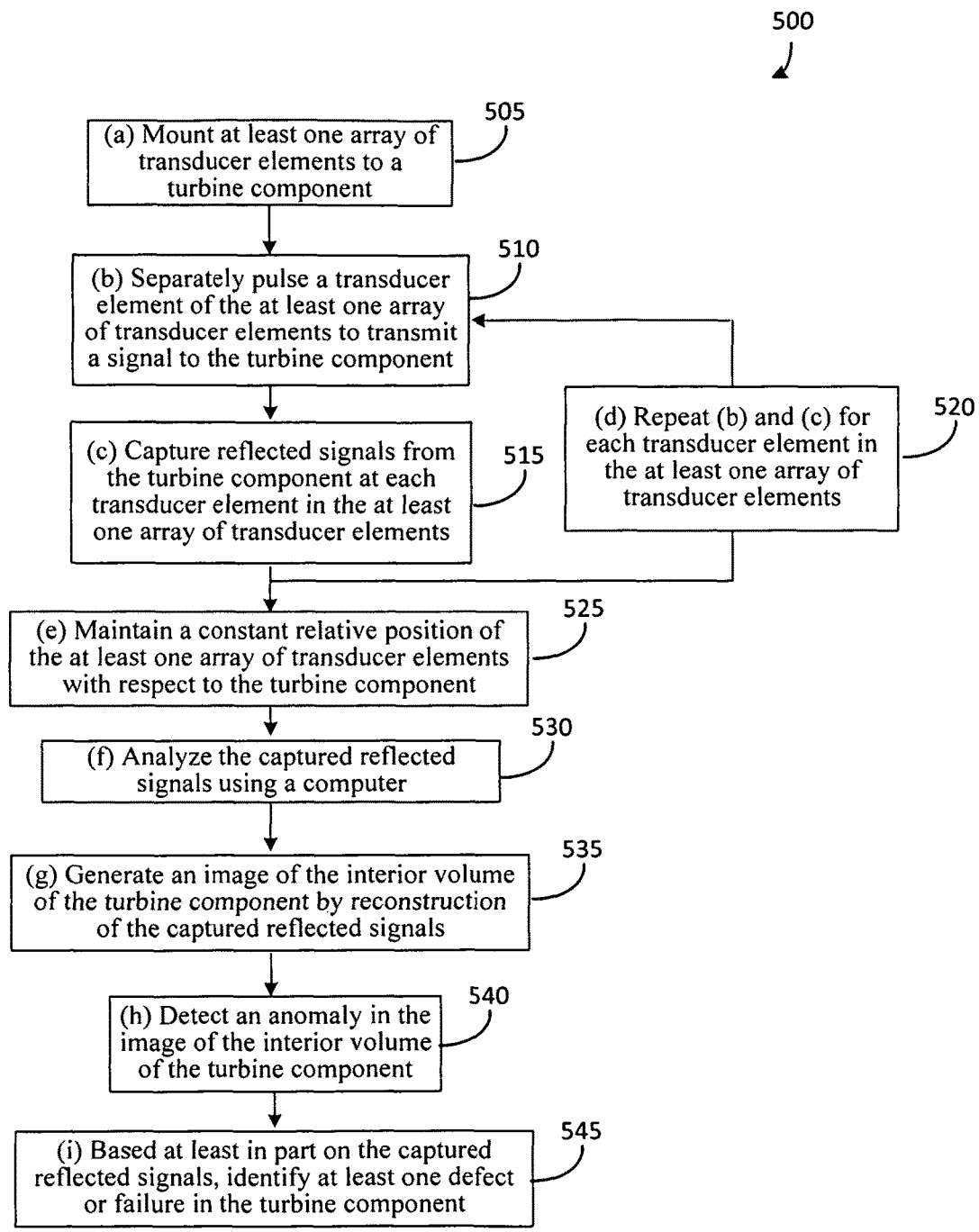

FIG. 5 illustrates an example flowchart of a method for ultrasonic inspection of a turbine component in accordance with certain embodiments of the disclosure.

DETAILED DESCRIPTION OF THE DISCLOSURE

The disclosure now will be described more fully hereinafter with reference to the accompanying drawings, in which example embodiments of the disclosure are shown. This disclosure may, however, be embodied in many different forms and should not be construed as limited to the example embodiments set forth herein; rather, these example embodiments, which are also referred to herein as "examples," are described in enough detail to enable those skilled in the art to practice the present subject matter. The example embodiments may be combined, other embodiments may be utilized, or structural, logical, and electrical changes may be made, without departing from the scope of the claimed subject matter. Like numbers refer to like elements throughout.

Generally, certain embodiments of the systems and methods described herein are directed to ultrasonic inspection of turbine components. In some example implementations, ultrasonic inspection may be used to evaluate a turbine that is operating or shut down, in order to identify various potential turbine component failures and/or defects that may adversely affect the operation of the turbine either currently and/or in the future.

Technical effects of certain embodiments of the disclosure can include reducing failures and downtime of a turbine by identifying failures or defects in a particular turbine component prior to an unplanned shutdown of the turbine. Further technical effects of certain embodiments of the disclosure can include reducing power unit downtime by eliminating or otherwise minimizing the need for costly replacement of a turbine component.

The following provides the detailed description of various example embodiments related to systems and methods for ultrasonic inspection of turbine components.

Referring now to FIG. 1, a block diagram illustrates an environment 100 for implementing certain methods and systems for ultrasonic inspection of turbine components, in accordance with one or more example embodiments. The system environment 100 may include a turbine component 110, such as a gas turbine or steam turbine component. For example, a gas turbine or steam turbine component can include, but may not be limited to, a turbine rotor, turbine wheel, turbine blade, or turbine casing. A system 105 according to an embodiment of the disclosure can include at least one array of transducer elements 120, ultrasonic instrumentation 130, and a computer 150. As shown in FIG. 1, at least one array of transducer elements 120 can be mounted to the turbine component 110 of interest. The at least one array of transducer elements 120 can be connected to the ultrasonic instrumentation 130. The computer 150 can be communicatively coupled to the ultrasonic instrumentation 130 via a communication interface 140, which can be any of one or more communication networks such as, for example, an Ethernet interface, a Universal Serial Bus (USB) interface, or a wireless interface. In certain embodiments, the computer 150 can be coupled to the ultrasonic instrumentation 130 by way of a hard wire or cable, such as a computer or network interface cable. For example, an Ethernet or USB cable can be used to connect the computer 150 and ultrasonic instrumentation 130. In other embodiments, additional system elements (not shown) can be included, such as an ultrasonic pulser-receiver, a matrix array controller, a digital oscilloscope as well as additional software for analysis and anomaly detection.

The at least one array of transducer elements 120 can be one or more arrays of transducer elements or probes. For example, transducer probes can include monocrystal transducer probes, dual-element transducer probes or multi-element phased array transducer probes. The ultrasonic instrumentation 130 can be one or more acquisition units for transmitting and capturing signals from the turbine component 110 of interest, an ultrasonic pulser-receiver, a matrix array controller, a digital oscilloscope, a motion control drive unit or a transducer scanner.

The computer 150 can be a computer system having a processor(s) that executes programs to control the operations of the ultrasonic instrumentation 130 and the array of transducer elements 120, provides inputs, gathers transfer function outputs, and transmits instructions from human operators.

The computer 150 can also interact with the ultrasonic instrumentation 130 to provide notifications concerning possible anomalies of the turbine component 110 to an operator or another user, based on which preventive action can be taken, and so forth. In some embodiments, the ultrasonic instrumentation 130 may reside as part of the computer 150. Alternatively, the computer 150 can be an independent entity communicatively coupled to the ultrasonic instrumentation 130.

In accordance with an embodiment of the disclosure, a full matrix capture approach to ultrasonic inspection of a turbine component can be implemented. With respect to FIG. 1, each transducer element of the at least one array of transducer elements 120 can be pulsed separately to transmit a signal to the turbine component 110 of interest. The reflected signals from the turbine component 110 can be captured at each transducer element in the at least one array of transducer elements 120, and communicated to the computer 150. During the signal transmission and capturing of reflected signals, the at least one array of transducer elements 120 can be maintained at a constant relative position with respect to the turbine component 110.

The captured reflected signals communicated to the computer 150 can be analyzed using one or more suitable methods, and an image of an interior volume of the turbine component 110 can be generated by reconstruction of the captured reflected signals. The computer 150 can utilize any number of software and/or hardware modules to detect anomalies in the image of the interior volume of the turbine component 110, which can help identify defects and/or failures in the turbine component 110. Using this information, a failure of the turbine component 110 can be detected at a relatively early stage, and corrective measures can be taken to prevent or otherwise minimize relatively major or catastrophic failures and associated costs.

Referring now to FIG. 2A, in accordance with an embodiment of the disclosure, a rotor environment 200 can include a turbine rotor 210 and associated inspection regions 220 for implementing certain methods and systems for ultrasonic inspection of turbine components, in accordance with one or more example embodiments. For reference, various inspection regions 220 are labeled (1) through (4). Each inspection region shown can be part of a volume of the rotor geometry to be scanned. Referring now to the view of inspection region (1) in FIG. 2B, a 3-D view of the inspection region (1) 230 can include a transducer element 232 and an interior volume 234. The interior volume 234 can represent the three dimensional scanning volume whose image can be generated by digital reconstruction of the captured reflected signals. The transducer element 232 can be part of the array of transducer elements 120 that can be mounted on the turbine rotor 210. As illustrated in FIG. 2C, a possible scanning configuration 240 is shown. While one possible scanning configuration 240 is illustrated, several other possible scanning configurations can be implemented in various embodiments of the disclosure.

Referring now to FIG. 3A, in accordance with some embodiments of the present disclosure, at least one array of transducer elements 120 is mounted to a turbine component, such as 110 in FIG. 1. As shown in the figure, the at least one array of transducer elements 120 can include transducer elements or probes 305 numbered 1 to n. Each transducer element 305 acts as a transmitter 320 and a receiver 330.

During the full matrix capture process, each transducer element 305 can be pulsed to transmit an ultrasonic signal to the turbine component (not shown). Each transducer element 305 of the array of transducer elements 120 captures the reflected signals from the turbine component. The captured reflected signals at each transducer element 305 can be recorded and stored for post-processing. A second, third, fourth and so on transducer element 305 can then be pulsed in sequence until all of the n transducer elements have been pulsed and the captured reflected signals from the turbine component from all of the n elements have been recorded and stored for post-processing.

The full matrix process illustrated above can result in a two dimensional transducer element matrix (n by n) 310 as shown in FIG. 3B, where each receiving transmitter element (receiver 330) can receive and store signals from the pulse from each transmitting element (transmitter 320). The two dimensional transducer element matrix 310 can allow for three dimensional scanning of the interior volume, such as 234 in FIG. 2B. In various embodiments, the three dimensional scanning of the interior volume 234 can be used to reconstruct an image of the interior volume 234 of the turbine component 110 using captured reflected signals from multiple beam angles, such as, for example, scanning with various skew (azimuth) and theta (refracted) beam angles.

Referring again to the two dimensional transducer element matrix 310 of FIG. 3B, the data received from each element of the two dimensional transducer element matrix 310 can be recorded as a time series. The resultant data signal from each transmitting element (transmitter 320) can be captured by each receiving element (receiver 330) over time and can be a three dimensional matrix of n by n by time samples.

The above description of the matrix in FIG. 3B illustrates data captured using a pulse-echo mode, where each transducer element 305 can transmit a signal and receive the reflected signal from the turbine component 110. In another embodiment, data can be captured in a similar matrix using a pitch-catch mode, where one set of transducer elements 305 or one array of transducer elements 120 can be used to transmit signals (transmitter 320), while another set of transducer elements 305 or another array of transducer elements 120 can act as receiver elements (receiver 330).

Attention is now drawn to FIG. 4, which illustrates an example computer system 150 configured for implementing a system and method for ultrasonic inspection of a turbine component 110 in accordance with certain embodiments of the disclosure. The computer system can incorporate a processor 405 for executing certain operational aspects associated with implementing certain systems and methods for ultrasonic inspection of a turbine component 110 in accordance with certain embodiments of the disclosure. The processor 405 can be capable of communicating with a memory 425. The processor 405 can be implemented and operated using appropriate hardware, software, firmware, or combinations thereof. Software or firmware implementations can include computer-executable or machine-executable instructions written in any suitable programming language to perform the various functions described. In one embodiment, instructions associated with a function block language can be stored in the memory 425 and executed by the processor 405.

The memory 425 can be used to store program instructions that are loadable and executable by the processor 405, as well as to store data generated during the execution of these programs. Depending on the configuration and type of the computer system 150, the memory 425 can be volatile (such as random access memory (RAM)) and/or non-volatile (such as read-only memory (ROM), flash memory, etc.). In some embodiments, the memory devices can also include additional removable storage 430 and/or non-removable storage 435 including, but not limited to, magnetic storage, optical disks, and/or tape storage. The disk drives and their associated computer-readable media can provide non-volatile storage of computer-readable instructions, data structures, program modules, and other data for the devices. In some implementations, the memory 425 can include multiple different types of memory, such as static random access memory (SRAM), dynamic random access memory (DRAM), or ROM.

The memory 425, the removable storage 430, and the non-removable storage 435 are all examples of computer-readable storage media. For example, computer-readable storage media can include volatile and non-volatile, removable and non-removable media implemented in any method or technology for storage of information such as computer-readable instructions, data structures, program modules or other data. Additional types of computer storage media that can be present include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile discs (DVD) or other optical storage, magnetic cassettes, magnetic tapes, magnetic disk storage or other magnetic storage devices, or any other medium which can be used to store the desired information and which can be accessed by the devices. Combinations of any of the above should also be included within the scope of computer-readable media.

Computer system 150 can also include one or more communication connections 410 that can allow a control device (not shown) to communicate with devices or equipment capable of communicating with the computer system 150. The communication connection(s) 410 can include communication interface 140. Connections can also be established via various data communication channels or ports, such as USB or COM ports to receive cables connecting the control device to various other devices on a network. In one embodiment, the control device can include Ethernet drivers that enable the control device to communicate with other devices on the network. According to various embodiments, communication connections 410 can be established via a wired and/or wireless connection on the network.

The computer system 150 can also include one or more input devices 415, such as a keyboard, mouse, pen, voice input device, gesture input device, and/or touch input device. It can further include one or more output devices 420, such as a display, printer, and/or speakers.

In other embodiments, however, computer-readable communication media can include computer-readable instructions, program modules, or other data transmitted within a data signal, such as a carrier wave, or other transmission. As used herein, however, computer-readable storage media does not include computer-readable communication media.

Turning to the contents of the memory 425, the memory 425 can include, but is not limited to, an operating system (OS) 426 and one or more application programs or services for implementing the features and aspects disclosed herein. Such applications or services can include an anomaly detection module 427 for executing implementing systems and methods for ultrasonic inspection of a turbine component 110. In one embodiment, the anomaly detection module 427 can be implemented by software that is provided in configurable control block language and is stored in non-volatile memory. When executed by the processor 405, the anomaly detection module 427 can implement the various functionalities and features associated with the computer system 150 described in this disclosure.

FIG. 5 illustrates an example flowchart 500 of a method for ultrasonic inspection of turbine components according to at least one embodiment of the disclosure. The flowchart 500 represents a series of operations that can be executed by the interaction of the various functional blocks shown in FIG. 1. More particularly, the flowchart 500 includes a block 505 representing an operation to mount at least one array of transducer elements 120 to a turbine component 110. In block 510, a transducer element 305 of the at least one array of transducer elements 120 can be separately pulsed to transmit a signal to the turbine component 110. In block 515, the reflected signals from the turbine component 110 can be captured at each transducer element 305 of the at least one array of transducer elements 120. In block 520, the pulsing and capturing of signals described in blocks 510 and 515 can be repeated for each transducer element 305 of the at least one array of transducer elements 120. In block 525, the at least one array of transducer elements 120 can be maintained at a constant relative position with respect to the turbine components during the processes associated with blocks 505, 510, 515 and 520. In block 530, the captured reflected signals can be analyzed using a computer 150. Different methods of analysis in the full matrix capture can be implemented, such as, for example, utilizing a total focusing method. In block 535, an image of the interior volume 234 of the turbine component 110 can be generated by reconstruction of the captured reflected signals. In block 540, an anomaly in the image of the interior volume 234 of the turbine component 110 can be detected using suitable methods, such as, for example, the anomaly detection module 427 of the computer system 150. In block 545, based at least in part on the captured reflected signals, at least one defect or failure in the turbine component 110 can be identified. This information can be communicated via the computer system 150 so that appropriate actions can be taken to repair or replace the turbine component 110.

References are made herein to block diagrams of systems, methods, and computer program products according to example embodiments of the disclosure. It will be understood that at least some of the blocks of the block diagrams, and combinations of blocks in the block diagrams, respectively, can be implemented at least partially by computer program instructions. These computer program instructions can be loaded onto a general purpose computer, special purpose computer, a special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions can also be stored in a computer-readable memory that can direct a computer or other programmable data processing apparatus to function in a particular manner, such that the instructions stored in the computer-readable memory produce an article of manufacture including instruction means that implement the function specified in the block or blocks. The computer program instructions can also be loaded onto a computer or other programmable data processing apparatus to cause a series of operational elements to be performed on the computer or other programmable apparatus to produce a computer implemented process such that the instructions that execute on the computer or other programmable apparatus provide elements for implementing the functions specified in the block or blocks.

One or more components of the systems and one or more elements of the methods described herein can be implemented through an application program running on an operating system of a computer. They also can be practiced with other computer system configurations, including handheld devices, multiprocessor systems, microprocessor based, or programmable consumer electronics, mini-computers, mainframe computers, etc.

Application programs that are components of the systems and methods described herein can include routines, programs, components, data structures, etc., that implement certain abstract data types and perform certain tasks or actions. In a distributed computing environment, the application program (in whole or in part) can be located in local memory, or in other storage. In addition, or in the alternative, the application program (in whole or in part) can be located in remote memory or in storage to allow for circumstances where tasks are performed by remote processing devices linked through a communications network.

Many modifications and other embodiments of the example descriptions set forth herein to which these descriptions pertain will come to mind having the benefit of the teachings presented in the foregoing descriptions and the associated drawings. Thus, it will be appreciated that the disclosure may be embodied in many forms and should not be limited to the example embodiments described above. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A system for ultrasonic inspection of a turbine component, the system comprising:
at least one array of transducer elements mounted on the turbine component and operable to (a) separately pulse a transducer element of the array of transducer elements to transmit a first signal to the turbine component, wherein reflected signals from the turbine component are directed towards two or more of the transducer elements in the at least one array of transducer elements, (b) capture the reflected signals from the turbine component at two or more of the transducer elements in the array of transducer elements, (c) repeat (a) and (b) in turn for each of the other transducer elements in the array of transducer elements, and (d) based at least in part on (a), (b) and (c), generate a two-dimensional transducer element matrix, wherein the mounted array of transducer elements is maintained in a constant relative position with respect to the turbine component while the turbine is in operation, the turbine component comprising at least one of a gas turbine rotor, a turbine wheel, and a turbine blade; and
a computer operable to analyze the capture reflected signals, generate an image of an interior volume of the turbine component based at least in part by reconstruction of the captured reflected signals and the two-dimensional transducer element matrix, and based at least in part based on the captured reflected signals and the two-dimensional transducer element matrix, identify at least one defect or failure in the turbine component.

2. The system of claim 1, wherein the computer comprises at least one of the following: an ultrasonic pulser-receiver, a matrix array controller, or a digital oscilloscope.

3. The system of claim 1, wherein the captured reflected signals comprise reflected signals with respective beam angles.

4. The system of claim 1, wherein the at least one array of transducer elements comprises multi-element phased array transducers in a pulse-echo mode.

5. The system of claim 1, wherein the at least one array of transducer elements comprises multiple arrays of transducer elements comprising multi-element phased array transducers in a pitch-catch mode.

6. The system of claim 1, wherein operations (a), (b) and (c) comprise a full matrix capture method.

7. A method for ultrasonic inspection of a turbine component, the method comprising:
(a) mounting at least one array of transducer elements to the turbine component;
(b) separately pulsing a transducer element of the at least one array of transducer elements to transmit a first signal to the turbine component, wherein reflected signals from the turbine component are directed towards two or more of the transducer elements in the at least one array of transducer elements;
(c) capturing the reflected signals from the turbine component at two or more of the transducer elements in the at least one array of transducer elements;
(d) repeating (b) and (c) in turn for each of the other transducer elements in the at least one array of transducer elements;
(e) based at least in part on (b), (c) and (d), generating a two-dimensional transducer element matrix;
(f) maintaining a constant relative position of the array of transducer elements with respect to the turbine component while the turbine is in operation, the turbine component comprising at least one of a gas turbine rotor, a turbine wheel, and a turbine blade; and
(g) based at least in part on the captured reflected signals and the two-dimensional transducer element matrix, identifying at least one defect or failure in the turbine component.

8. The method of claim 7, wherein the identifying at least one defect or failure in the turbine component comprises:
analyzing the captured reflected signals and the two-dimensional transducer element matrix using a computer;
generating an image of an interior volume of the turbine component by reconstruction of the captured reflected signals; and
detecting an anomaly in the image of the interior volume of the turbine component.

9. The method of claim 7, wherein the captured reflected signals comprise reflected signals with respective beam angles.

10. The method of claim 7, wherein analyzing the captured reflected signals comprises a total focusing method.

11. The method of claim 7, wherein the at least one array of transducer elements comprises multi-element phased array transducers.

12. The method of claim 7, wherein operations (b), (c) and (d) comprise a full matrix capture method.

13. A method for ultrasonic inspection of a turbine component, the method comprising:
(a) mounting at least one array of transducer elements to the turbine component;
(b) separately pulsing a transducer element of the at least one array of transducer elements to transmit a first signal to the turbine component, wherein reflected signals from the turbine component are directed towards two or more of the transducer elements in the at least one array of transducer elements;
(c) capturing the reflected signals from the turbine component at two or more of the transducer elements in the at least one array of transducer elements;
(d) repeating (b) and (c) in turn for each of the other transducer elements in the at least one array of transducer elements;
(e) based at least in part on (b), (c) and (d), generating a two-dimensional transducer element matrix;
(f) maintaining a constant relative position of the array of transducer elements with respect to the turbine component while the turbine is in operation, the turbine component comprising at least one of a gas turbine rotor, a turbine wheel, and a turbine blade;
(g) analyzing the captured reflected signals and the two-dimensional transducer element matrix using a computer;
(h) generating an image of the interior volume of the turbine component based at least in part by reconstruction of the captured reflected signals and the two-dimensional transducer element matrix; and
(i) based at least in part on detecting an anomaly in the image of the interior volume of the turbine component, identifying at least one defect or failure in the turbine component.

14. The method of claim 13, wherein the captured reflected signals comprise reflected signals from respective beam angles.

15. The method of claim 13, wherein analyzing the captured reflected signals comprises a total focusing method.

16. The method of claim 13, wherein the at least one array of transducer elements comprises multi-element phased array transducers.

17. The method of claim 13, wherein operations (b), (c) and (d) comprise a full matrix capture method.

* * * * *